US005780613A

United States Patent [19]
Letsinger et al.

[11] Patent Number: 5,780,613
[45] Date of Patent: Jul. 14, 1998

[54] COVALENT LOCK FOR SELF-ASSEMBLED OLIGONUCLEOTIDE CONSTRUCTS

[75] Inventors: Robert L. Letsinger, Wilmette, Ill.; Mathias K. Herrlein, Frankfurt, Germany

[73] Assignee: Northwestern University, Evanston, Ill.

[21] Appl. No.: 509,858

[22] Filed: Aug. 1, 1995

[51] Int. Cl.[6] .............................. C07H 21/04; C12Q 1/68
[52] U.S. Cl. ........................ 536/25.33; 435/6; 536/22.1; 536/23.1; 536/25.3
[58] Field of Search ............................... 435/6; 536/22.1, 536/23.1, 25.3, 25.33

[56] References Cited

PUBLICATIONS

Herrlein and Letsinger, "A Covalent Lock for Self-Assembled Oligonucleotide Conjugates" *J. Am. Chem. Soc.*, 117:10151–10152 (1995).
Ashley and Kushlan, "Chemical synthesis of oligoeoxynucleotide dumbbells" *Biochemistry*, 30:2927–2933 (1991).
Barone et al., "In situ activation of bis–dialkylaminophosphines —a new method . . . " *Nucleic Acids Res.*, 12:4051–4061 (1984).
Bischofberger and Wagner, "Antisense approaches to antiviral agents" *Virology*, 3:57–66 (1992).
Chaturvedi and Letsinger, "Novel properties of oligonucleotides containing a steroid bridge" Am. Chem. Soc. Meeting in Anaheim, CA, Apr. 1995.
Chladek and Nagyvary, "Nucleophilic reactions of some nucleoside phosphorothioates" *J. Am. Chem. Soc.*, 94:2079–2085 (1972).
Cook. "Nucleoside S–alkyl phosphorothioates. IV. Synthesis of nucleoside phosphorothioate monoesters" *J. Am. Chem. Soc.*, 92:1090–195 (1970).
Crooke and Leblau, Ed., *Antisense Research and Application*. CRC Press, Boca Raton, Florida.
Durand et al., "Circular dichrioism studies of an oligodeoxy–ribonucleotide containing a hairpin loop" *Nucleic Acids Res.*, 18:6353–6359 (1992).
Erie et al., "A dumbell–shaped, double–hairpin structure of DNA: a thermodynamic investigation" *Biochemistry*, 26:7150–71 (1989).
Fu et al., "Hammerhead ribozymes containing non–nucleoside linkers are active RNA catalysts" *Am. Chem. Soc.*, 116:4591–4598 (1994).
Gao et al., "Double–stranded cyclic oligonucleotides with non–nucleotide bridges" *Bioconjugate Chem.*, 5:445–453 (1994).
Giver et al., "Selective optimization of the Rev–binding element of HIV–1" *Nucleic Acids Res.*, 21:5509–5516 (1993).
Goodwin and Lynn, "Template–directed synthesis: use of a reversible reaction" *J. Am. Chem. Soc.*, 114:9197–9198 (1992).
Gryaznov, "Autoligation of oligonucleotides via nucleophilic substitution reaction" *Nucleosides and Nucleotides*, 14:1019–1022 (1995).

Gryaznov and Letsinger, "Synthesis and properties of oligonucleotides containing aminodeoxythymidine units" *Nucleic Acids Research*, vol. 20, No. 13, pp. 3403–3409 (1992).
Gryaznov and Letsinger, "Chemical ligation of oligonucleotides in the presence and absence of a template" *J. Am. Chem. Soc.*, 115:3808–3809 (1993).
Gryaznov and Letsinger, "Template controlled coupling and recomination of oligonucleotide blocks . . ." *Nucleic Acids Res.* 21:1403–1408 (1993).
Gryaznov et al., "Enhancement of selectivity in recognition of nucleic acids via chemical autoligation" *Nucleic Acids Res.*, 22:2366–2369 (1994).
Helene and Toulme, "Specific regulation of gene expression by antisense, sense and antigen nucleic acids" *Biochem. Biophys. Acta*, pp. 99–125 (1990).
Heller and Tullis, "Self–organizing molecular photonic structures based on functionalized synthetic nucleic acid (DNA) polymers" *Nanotechnology*, 2:165–171 (1991).
Herrlein and Letsinger, "Selective chemical autoligation on a double–stranded DNA template" *Nucleic Acids Res.*, 22:5076–5078 (1994).
Kool, "Molecular recognition by circular oligonucleotides: increasing the selectivity of DNA binding" *J. Am. Chem. Soc.*, 113:6265–6266 (1991).
Kresse et al., "The use of S–2–cyanoethyl phosphorothioate in the preparation of oligo 5'–deoxy–5"–thiothymidylates" *Nucleic Acids Res.*, 2:1–9 (1975).
Letsinger et al., "Use of hydrophobic substituents in controlling self–assembly of oligonucleotides" *J. Am. Chem. Soc.*, 115:7535 (1993).
Letsinger and Wu, "Use of a stilbenedicarboxaminde bridge in stabilizing, monitoring, and photchemically . . . " *J. Am. Chem. Soc.*, 117:7323–7328 (1995).
Lewis et al., "Hybrid oligonucleotide containing stilbene units. Excimer fluorescence and photodimerization" *Am. Chem. Soc.*, 117:8785–8792 (1995).
Lowe, "Clinical applications of gene probes in human genetic disease, malignancy, and infectious disease" *Clinica Chimica Acta*, 157:1–32, (1986).
Luebke and Dervan, "Nonenzymatic sequence–specific ligation of double–helical DNA" *J. Am. Chem. Soc.*, 113:7447–7448 (1991).
Luebke and Dervan, "Nonenzymatic ligation of double–helical DNA by alternate–brand triple helix formation" *Nucleic Acids Res.*, 20:3005–3009 (1992).
Ma et al., "Design and synthesis of RNA miniduplexes via a synthetic linker approach" *Biochemistry*, 32:1751–1758 (1993).

(List continued on next page.)

*Primary Examiner*—Lisa B. Arthur
*Attorney, Agent, or Firm*—Kohn & Associates

[57] ABSTRACT

A method of autoligating self-assembled oligonucleotide blocks is disclosed. The method includes the step of displacing a 5' displaceable group by a 3' thiophosphoryl group to form an —OP(O)(O$^-$)S— internucleoside linkage.

10 Claims, 7 Drawing Sheets

PUBLICATIONS

Meade and Kayyem, "electron transfer through DNA: site–specific modification of duplex DNA with ruthenium donors and acceptors" *Agnew. Chem. Int. Ed. Engl.* 34:352–354 (1995).

Paterson, "Current flow in DNA could lead to faster genetic testing" *Scientific American*, 33–34 (1995).

Salunkhe et al., "Control of folding and binding of oligonucleotides by use of nonnucleotide linker" *J. Am. Chem. Soc.*, 114:8768–8772 (1992).

Shabarova, "Chemical development in the design of oligonucleotide probes for binding to DNA and RNA" *Biochimie*, 70:1323–1334 (1988).

Thomson et al., *Nucleic Acids Res.*, 21:5600–5603 (1993).

Uhlman and Peyman, "Antisense oligonucleotides: a new therapeutic principle" *Chem. Rev.*, 90:544–584 (1990).

Urea et al., "A comparison on non–radioisotopic hybridization assay methods using fluorescent, chemiluminescent . . ." *Nucleic Acids Res.*, 16:4937–4956 (1988).

Kanaya and Yanagawa, "Template–directed polymerization of oligoadenylates using cyanogen bromide" *Biochemistry*, 25:7423–7430 (1986).

ically, such as by DNA ligase. A disadvantage of this method is that yields are variable and may be inefficient, depending upon the specific oligonucleotide sequences. Also, a close fit of the oligomers to be ligated is required. Such prior art methods of ligation are ill suited for locking unusual assemblies that fit loosely at the termini to be ligated.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGGAAGAAGC GGAGAC        16

( 2 ) INFORMATION FOR SEQ ID NO:2:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTCTCCGC        8

( 2 ) INFORMATION FOR SEQ ID NO:3:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTCTTCCT        8

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTCTCCGCTT CTTCCT        16

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: both ( x i ) SEQUENCE DESCRIPTION: SEQ ID NO:5:

TTCCTTTTGG AATTCCTTTT GGAA        24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: both ( x i ) SEQUENCE DESCRIPTION: SEQ ID NO:6:

TGGGCGCAGC TGACGGTACA CCGG        24

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTTTTTTTTT TT        12

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:8:

AAAAAAAAA AA                                                               12

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

GGUGGGCGCA GCUUGCGCUG ACGGUACACC                         30

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

GUGGGCGCAG CUGACGGUAC AC                                   22

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: circular (xi) SEQUENCE DESCRIPTION: SEQ ID NO:11:

UGGGCGCGGU ACA                                                     13

COVALENT LOCK FOR SELF-ASSEMBLED OLIGONUCLEOTIDE CONSTRUCTS

This invention was made with Government support from the National Institute of General Medical Sciences (GM 10265) and the National Institute of Allergy and Infectious Diseases (Grant UOI AI24846). The Government has certain rights in the invention.

TECHNICAL FIELD

The present invention relates to hybridization dependent autoligation for forming oligonucleotide conjugates and the product of the reactions, the products having use in diagnostic methods for diseases or disorders involving mutation in nucleic acid sequences as in well therapeutic applications of oligonucleotides.

BACKGROUND OF THE INVENTION

Synthetic oligonucleotides are extensively used as sequence specific antisense agents (Helene, 1990; Uhlman, 1990; Crooke, 1993), as well as probes for hybridization based detection assays of nucleic acids (Lowe 1986; Urdea 1988). Antisense oligonucleotides have also demonstrated potential as new types of therapeutic agents for treating such diseases and disorders as viral diseases, cancer, genetic disorders, as well as other diseases and disorders (Bischofberger and Wagner, 1992).

A different approach involving current research in chemistry is directed towards the design and study of self-assembling supramolecular systems. Oligonucleotide conjugates (oligonucleotide linked covalently to non-nucleotide organic groups or domains) have high potential for applications in this area. Oligonucleotide segments can serve as structural elements to organize and place large organic fragments that serve as reporter groups, catalytic agents, hydrophobic binding pockets, energy transfer relays, etc. in predetermined position. Examples of such organization are provided by oligonucleotide-stilbene dicarboxamides (Letsinger and Wu, 1994, 1995; Lewis et al., in press; Chaturvedi et al., 1995). Examples of oligonucleotide-androstanediol conjugates are disclosed in S. Chaturvedi and R. L. Letsinger, Am. Chemical Soc. meeting in Anaheim, Calif. April 1995.

In addition, organic groups can function as bridges between oligonucleotide strands to stabilize double and triple helical oligonucleotide complexes as discussed in Durand et al. 1992; Shlunkhe et al. 1992. Such conjugates have utility as small oligonucleotide decoys to inhibit viral replication as discussed in Ma et al. 1993. Oligonucleotide conjugates can also be used in constructing catalysts (Thompson et al. 1993; Fu et al. 1994), and as components in nanoscale photonic and electronic devices (Heller et al., 1991; Meade et al. 1995; Paterson et al. 1995).

The supramolecular systems discussed above are all based on oligonucleotide hybrids which are all formed reversibly. For many purposes, it is desirable to irreversibly lock the system in place by covalent bonds after the self-assembly process so that the structure will not fall apart at a later time.

Ligation reactions of oligonucleotides in the prior art are usually effected enzymatically, such as by DNA ligase. A disadvantage of this method is that yields are variable and may be inefficient, depending upon the specific oligonucleotide sequences. Also, a close fit of the oligomers to be ligated is required. Such prior art methods of ligation are ill suited for locking unusual assemblies that fit loosely at the termini to be ligated.

Recently, several chemical ligation procedures have been reported. Those that afford natural phosphodiester links require the addition of relatively harsh reagents, such as water soluble carbodiimide or cyanoimidazole (Shabarova, 1988; Luebke and Dervan, 1992), and the reactions are often slow and relatively inefficient (Ashley et al., 1991) and require a close fit of the functional groups to be ligated. Other chemical procedures provide internucleotide links such as —OP(O) (O$^-$)S—SP(O) (O$^-$)O— (Gryaznov and Letsinger, 1991), —OP(O) (O$^-$)—SCH$_2$C(O)NH— (Gryaznov and Letsinger, 1993), —CH$_2$CH$_2$—NH$_2^+$— (Goodwin and Lynn, 1992), and —NHC(O)CH$_2$S— (Gryaznov, 1995) that differ substantially from the natural phosphodiester link |—OP(O) (O$^-$)O—| and can lead to distortions and destablization of the organized structure. The Goodwin and Lynn coupling is slow, inefficient, and requires addition of a strong reducing agent (sodium borohydride) to stabilize the structure. The coupling leading to the S—S link is rapid and efficient; however, the internucleoside link that is formed is readily cleaved by phosphorothioate derivatives, so the products are formed reversibly. Also, this ligation requires addition of an oxidizing agent, such as iodine. The coupling to afford the —P(O) (O$^-$)SCH$_2$C(O) NH— is attractive since the reaction is rapid and efficient and does not require additional activating agents. However, the synthesis of the oligomers to be coupled is relatively complex. A protected amino nucleoside phosphoramidite reagent has to be synthesized and utilized in a solid support synthesis; then the oligomer has to be cleaved from the support and modified in solution after isolation. This method also suffers the disadvantage that the bromoacetylamino-oligonucleotide is relatively unstable in aqueous solution, so that storage of the oligomers poses a problem.

It would be desirable to have a method for ligating oligonucleotides, organized in dilute aqueous solution, efficiently and irreversibly with generation of internucleoside links that are very close in geometry and electronic characteristics to the natural phosphodiester link. Further, it would be preferable to utilize readily available reagents and to carry out the synthesis of the requisite oligonucleotides directly on a solid support without need for post synthetic modification to generate reactive functional groups. The ligation should depend on a specific organization, induced by base pairing, of the oligonucleotide or oligonucleotides; however, there should be sufficient flexibility in the system to permit ligation of unusual constructs that do not necessarily align the reactive functional groups as precisely as required for enzymatic ligation or chemical ligation leading to natural phosphodiester links. The prior art chemistry described above does not satisfy these criteria.

SUMMARY OF THE INVENTION

In accordance with the present invention, there is provided a method of autoligating self-assembled organized oligonucleotide blocks by displacing a 5' displaceable group by a 3' thiophosphoryl group to form an —OP(O)(O$^-$)S— internucleoside linkage. The present invention further provides a self-assembled assembled oligonucleotide domain comprising the covalent linkage of the formula —OP(O) (O$^-$)S—, the covalent linkage being the product of an autoligation.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5 shows that the reaction product elutes much sooner than the reactant on reversed phase chromatography (RP HPLC) as a consequence of loss of the lipophilic tosyl group, therefore the cyclization product and the reactant can be easily separated. In contrast, cyclization of an unmodified oligonucleotide with formation of a natural phosphodiester bond either by enzymatic means (Erie et al., 1989) or by chemical activation (Ashley and Kushlan, 1991) affords a product that elutes very near to the reactant and is difficult to isolate;

DETAILED DESCRIPTION OF THE INVENTION

Generally, the present invention relates to a method of autoligating self-assembled oligonucleotide blocks by displacement of a 5' displaceable group by a 3' thiophosphoryl group to form an —OP(O) (O⁻)S— internucleoside linkage that stabilizes the self-assembled system. The present invention can be used to ligate the ends of two separate oligonucleotides aligned on a template, to join two oligonucleotides that form a double helix, or to cyclize self-organizing single stranded oligonucleotides that possess both a 5' displaceable group and a 3' thiophosphoryl group. Hybridization by pairing of complementary bases contained in the oligonucleotide segments constitutes an important factor in the organization or self-assembly process. Appropriately positioned organic fragments, as exemplified by a terethalyl bridge (Salunke et al., 1992), a stilbenedicarboxamide bridge (Letsinger and Wu, 1995), pendant cholesteryl groups (Letsinger et al., 1993), and androstanediol substituents (Chaturvedi and Letsinger, 1995) can also be exploited in creating self assembling systems containing oligonucleotide segments that undergo the ligation reaction.

Figure 12:
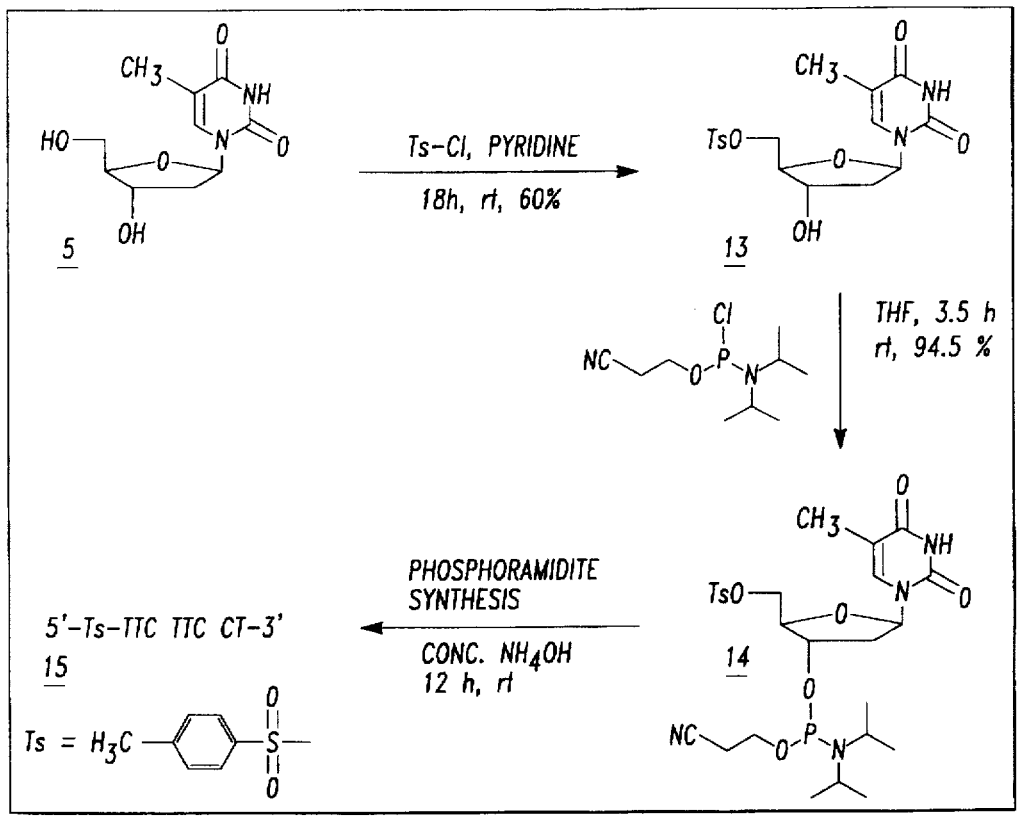
FIG. 12 illustrates the preparation and use of 5' tosylnucleoside phosphoramidate reagent and in synthesis of 5' tosyloligonucleotides (SEQ ID NO:3)

The displaceable group is an atom or group attached to carbon such that on nucleophilic attack on the carbon atom by sulfur of the thiophosphoryl group the displaceable group leaves as an anion. Results can be obtained with displaceable groups within a wide range of activities, as demonstrated by highly efficient couplings for oligomers ranging from a very slowly reacting 5'-chloro-5'deoxynucleoside derivative to a rapid reacting 5'O-p-nitrobenzenesulfonyl derivative. The p-toluenesulfonyl (tosyl) group is particularly well suited for these ligations. It is sufficiently reactive that the ligations in the organized systems proceed readily (within a few hours at 37° C.); but the reactivity is low enough that 5' O-tosyl oligonucleotides can be prepared on a solid support and cleaved from the support with concentrated ammonium hydroxide, with concomitant deblocking of the N-protecting groups, without damage to the 5' O-tosyl derivative. Since 5'O-tosylnucleosides can be readily prepared by direct tosylation of the nucleosides (Chladek and Nagyvary, 1972), and they can easily converted to cyanoethylphosphoramidite reagents by standard procedures, oligonucleotides containing 5' O-tosyl substituents can be easily prepared and isolated using standard solid support oligonucleotide chemistry. The synthetic chemistry is illustrated in FIG. 12. Other suitable displaceable groups can be selected from the Cl⁻, Br⁻, I⁻, and RSO₃ where R is phenyl or phenyl substituted with one to five atoms or groups comprising F, Cl, Br, I, alkyl (C1 to C6), nitro, cyano, sulfonyl and carbonyl, or R is alkyl with one to six carbons.

Figure 13:
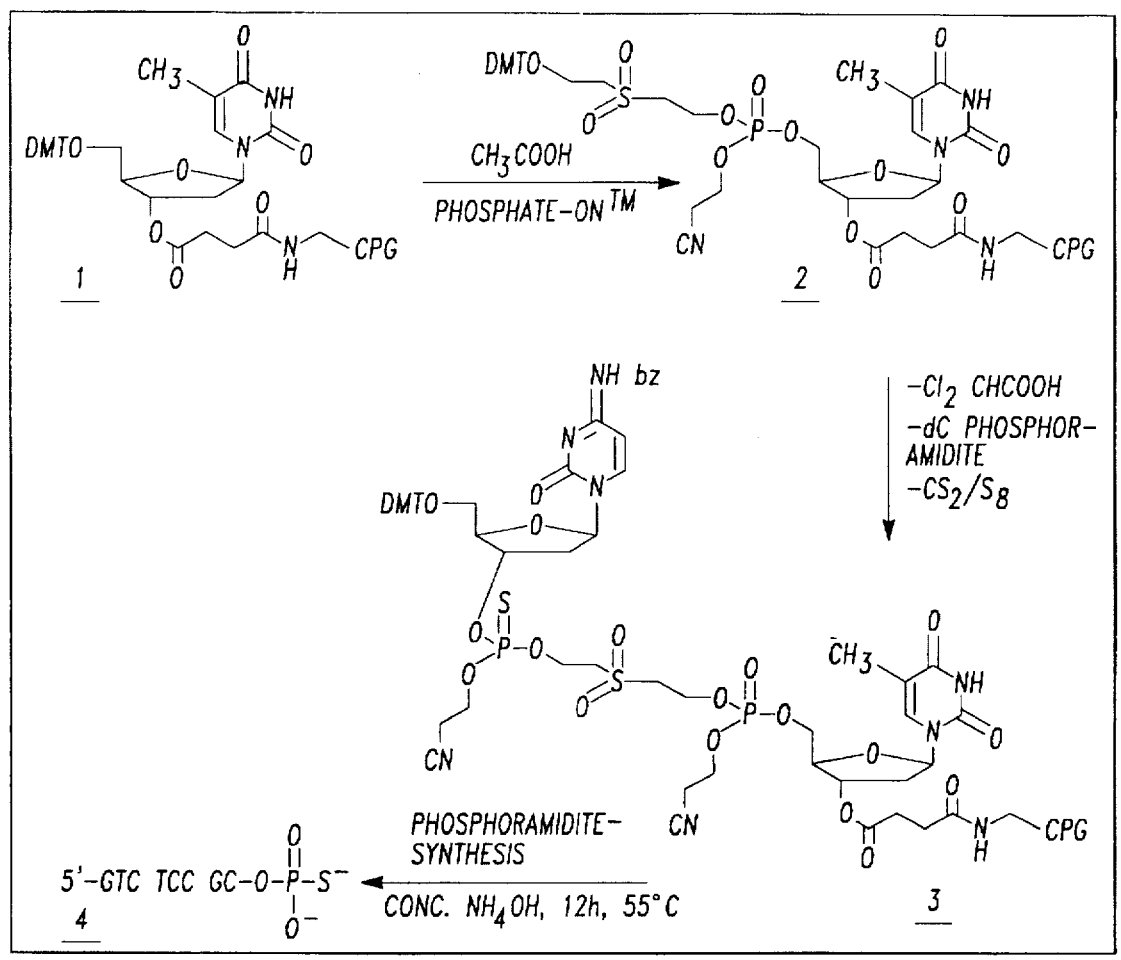
FIG. 13 illustrates the preparation of a 3'-phosphorothioate group wherein DMT is the demethoxytrityl group (SEQ ID NO:2), bz is the benzoyl group, and CPG is a controlled pore glass solid support anchored to the nucleotide.

The preparation of the 3' thiophosphoryl oligonucleotide derivatives is also straightforward (see Herrlein and Letsinger, 1994). As illustrated in FIG. 13, one starts with a commercially available nucleoside-loaded solid support, following coupling with a commercially available "Phosphate-ON™" phosphoramidite reagent and oxidation with sulfur, the DMT group is removed by standard treatment with dichloroacetic acid in methylene chloride and the nucleoside phosphoramidite reagent corresponding to the 3' terminal nucleoside of the oligonucleotide to be prepared is added. Conventional phosphoramidite chemistry is then employed to prepare the desired olioligonucleotide. At the end of the synthesis, cleavage with concentrated ammonium hydroxide liberates the desired oligonucleotide bearing a 3' thiophosphoryl group.

An important finding is that in dilute aqueous solutions the coupling reactions are exceedingly slow, but when the oligonucleotides are organized by intramolecular or intermolecular hybridization so that the reactive functional groups are in proximity, the reactions take place readily.

The new ligation scheme is illustrated hereinbelow by four different systems in which reversibly organized oligonucleotide segments are joined covalently, with resultant stabilization of the organized system, by the methods of this invention. These are discussed below with help of FIGS. 1–11 which show structures and present pertinent data. It may be noted, however, that the present invention can be utilized in various other systems as well, such as those disclosed in the copending application U.S. Ser. No. 08/436,145, filed May 8, 1995 which was allowed Mar. 19, 1996, relating to enhancement of selectivity of nucleic acid as well as those methods disclosed in the copending U.S. Ser. No. 08/376,291, filed Jan. 23, 1995 issued as U.S. Pat. No. 5,476,925, both of the aforementioned applications being assigned to the assignee of the present invention.

The criticality of the selection of the displaceable group is that displacement by the 3' thiophosphoryl group forms the specific —OP(O)(O⁻)S— internucleoside linkage. As demonstrated by the experimental section below, the method is distinguished from the prior art by having high efficiency of ligation, the absence of a requirement for any additional agents, such as enzymes or chemical activating reagents, ease of synthesis of oligonucleotide components, and the fact that the linker covalent bond that is generated, is very similar in geometry to the natural phosphodiester linkage. By being similar in geometry to the natural phosphodiester linkage, the linkage does not induce the backbone distortion characteristic of the extended bridges used in the prior art formed in the bromoacetylaminooligonucleotide couplings.

The experimental section below demonstrates that the tosyl-oligonucleotide is more stable in solution than the bromoacetylamino-oligonucleotide. This factor is particularly relevant in a commercial application since the modified oligonucleotide would have a longer shelf life.

It is critical that the 5' displaceable group and 3' thiophosphoryl group be brought to proximity allowing the displacement reaction of the 3' thiophosphoryl group for the displaceable group to form the above mentioned internucleoside linkage. This proximating step (step of bringing the reactive groups into proximity with each other), can be accomplished by methods known in the art such as those disclosed in the co-pending patent application, Ser. Nos. 08/436,145 and 08/376,291, incorporated herein by reference.

For example, non-bonded organic fragments comprising nucleic acids such as deoxyribonucleic acid having complementary base sequence or non-bonded organic fragments which can be non-complementary single stranded oligomers which are covalently coupled together their termini are aligned. By alignment, it is meant that in addition to using complementary sequences between the non-bonded organic fragments to align the individual oligomers, reactive groups, such as stilbene compounds, can be used to aid and facilitate the alignment and subsequent dimer formation between the oligomers. The use of reactive stilbene compounds bound to the oligomers provides an additional mechanism for preventing mismatching between the oligomers sought to be bound together.

In accordance with the aforementioned methods, a self-assembled oligonucleotide domain comprises the covalent linkage of the formula —OP(O)(O⁻)S—, the covalent linkage being the product of an autoligation. Such an oligonucleotide domain can be found in various oligonucleotide complexes and conjugates, as discussed above.

The utility of the present invention can be found for the use of such structural elements in the self assembling of supramolecular model systems as discussed in the background art section herein. That is, the present invention can be used to construct oligonucleotide segments that can serve as structural elements to organize and place larger organic fragments that serve as reporter groups, catalytic agents, hydrophobic binding pockets, and energy transfer relays at predetermined positions. References for such utilities are provided in the Background art section herein.

Figure 14:
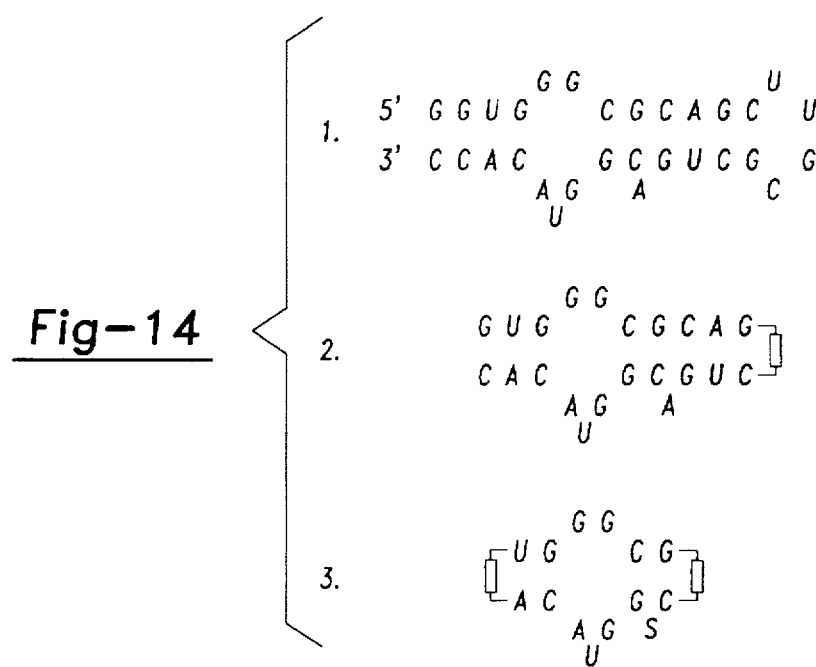
FIG. 14 illustrates small oligonucleotides (SEQ ID NO:9–11) which mimic the Rev binding element.

As a specific example of utility, the design of cyclized oligonucleotide conjugates that can serve as mimics of the Rev Responsive Element (RRE) in human immunodeficiency virus type 1 (HIV-1), a causative agent of AIDS. The Rev protein of HIV-1 is a regulatory protein required for gene expression of the virus. It functions by binding to a specific nucleotide sequence in the viral genome known as the Rev Responsive Element. The RRE has been mapped to a 234 nucleotide fragment of the HIV-1 genome, which is located within the env gene. In work aimed at further elucidating the chemistry of the interaction and to development of therapeutic agents, Ellington and coworkers (Giver, 1993) have recently demonstrated that a small hairpin oligonucleotide, termed a "Minimal Rev-binding Element" (RRE), bound the Rev protein with ~0.8 the binding affinity of the natural RRE (for structure see formula I in FIG. 14). Small molecules of this type therefore can serve as decoys for the Rev protein and be useful in studying and possibly in treating the AIDS disease. For work in cells and in living organisms, however, it is important that the oligonucleotide be as small as possible and still retain the conformation essential for binding the protein. In a related program we have synthesize a small oligonucleotide domain (see formula II in FIG. 14) stabilized by a stilbenedicarboxamide bridge. Although containing 8 fewer nucleotides than the minimal binding element, this construct was found to bind Rev effectively (~0.4 relative to 1 for a full 234-mer corresponding the natural binding site).

The new ligation reaction opens the possibility of synthesizing even small oligonucleotide conjugates which are further stabilized by cyclization and still maintain properly organized duplex and looped out segments. We have demonstrated that such cyclization and stabilization can indeed be realized by synthesizing a mimic in the deoxyribonucleotide series (compound 4, FIG. 6). On ring closure the stability of the organized system increased dramatically (over 40° C. increase in Tm in 0.1M NaCl). Ribonucleotide analogs of this and even smaller cyclic systems should also retain organized conformations and therefore be useful in studying and treating AIDS. Enzymatic and chemical ligation reactions that give natural phosphodiester bonds would be inapplicable here since they require a precise orientation of the phosphate and hydroxyl groups undergoing coupling. Other chemical methods leading to cyclization would give distorted linkages that should lead to distortion in the conformation required for binding of the Rev protein.

EXPERIMENTAL SECTION

The following examples demonstrate the advantages of the present invention and its use in three different systems requiring irreversible linkages.

General Methods

RP HPLC was carried out on a Hewlett Packard Hypersil ODS column, 4.6×200 mm, with 1%/minute gradient of 95:5 acetonitrile/0.03M triethylammonium acetate buffer. For ion exchange chromatography (IE HPLC) a Dionex NucleoPac PA-100, 4×250 mm column and a Dionex NucleoPac PA-100 guard column at pH 12 (10 mM NaOH) was used with a 2%/minute gradient of 1.0M NaCl in 10 mM NaOH>.

Melting curves were recorded using solutions 0.1M in NaCl, 10 mM in phosphate buffer at pH 7.0, 3 micromolar in oligonucleotide, by monitoring changes in absorbance at 260 nm while ramping the temperature at the rate of 1° C./minute.

Figure 1:
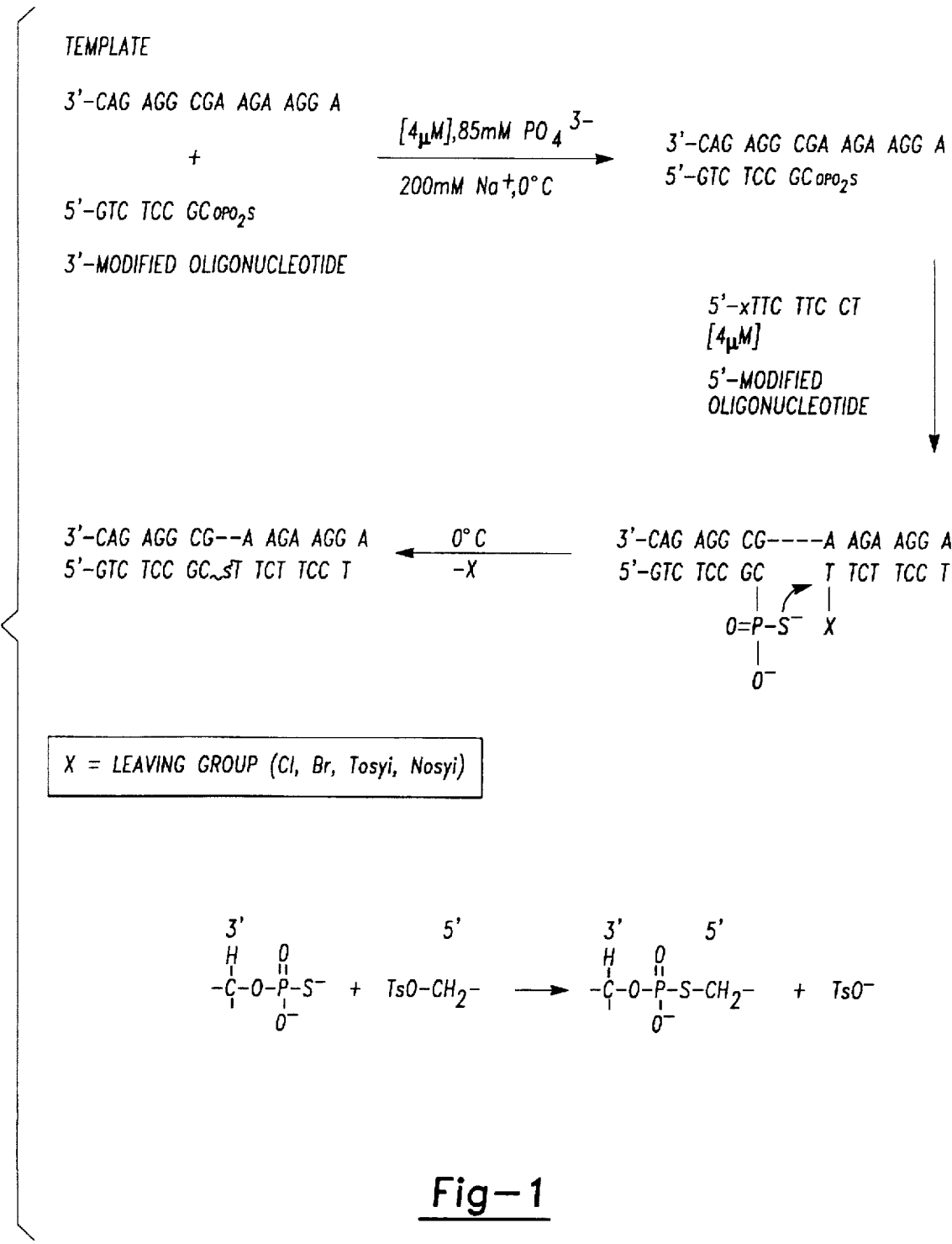
FIG. 1 is a diagram representing a ligation scheme in which an oligonucleotide containing a 3' phosphoryl group (SEQ ID NO:2) and another oligonucleotide (SEQ ID NO:2) containing a displaceable group at a terminal 5' carbon atom are aligned and ligated (SEQ ID NO:4) on a complementary template oligonucleotide (SEQ ID NO:1). The displaceable group, x, in these reactions is chloro, bromo, p-methylbenzenesulfonyl (tosyl), or p-nitrobenzenesulfonyl (nosyl)
Figure 2:
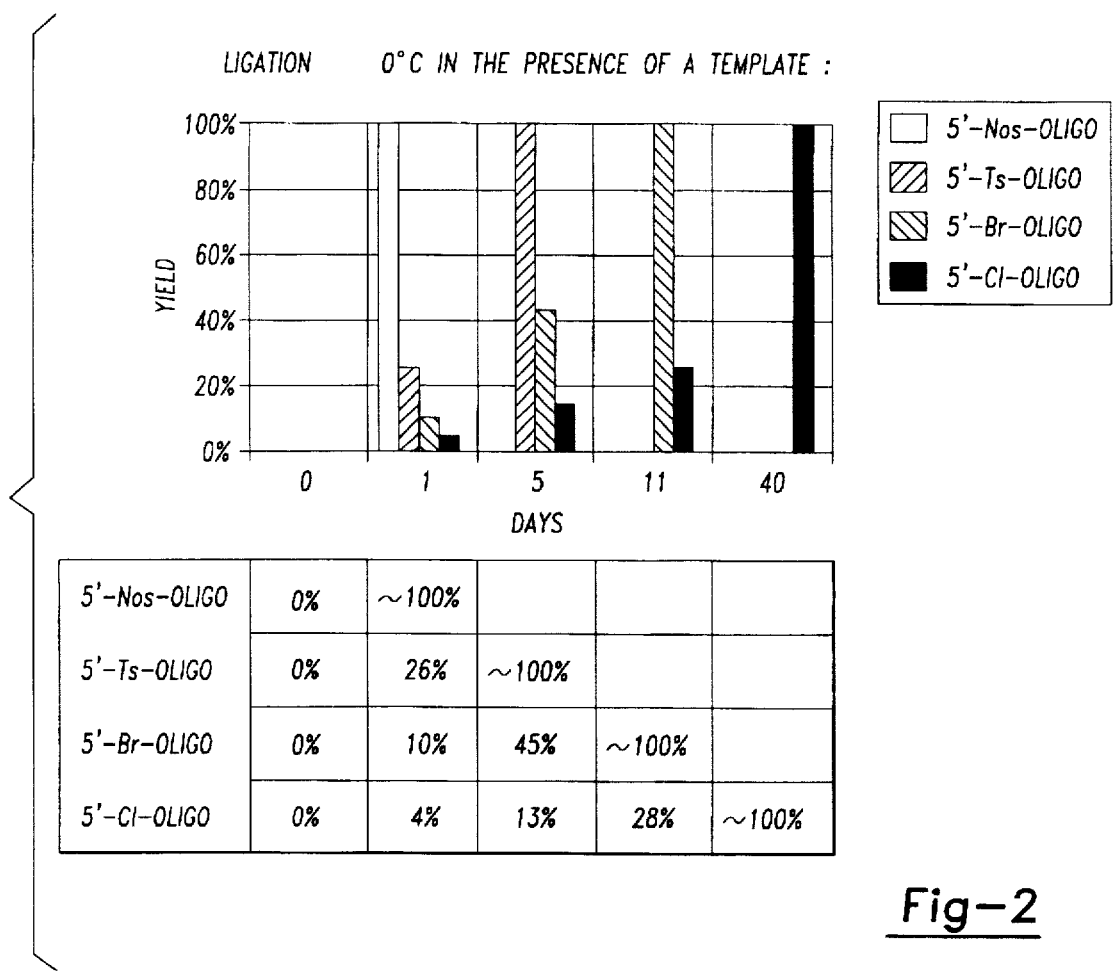
FIG. 2 is graph and table summarizing data from the experiments designated in FIG. 1. Each reaction proved to be slow at 0°, but the significant finding is that each proceeded cleanly to give close to a quantitative yield of the ligation product in the presence of the template. In absence of the template to align the oligonucleotides, coupling amounted to less than 1% in each case.
Figure 3:
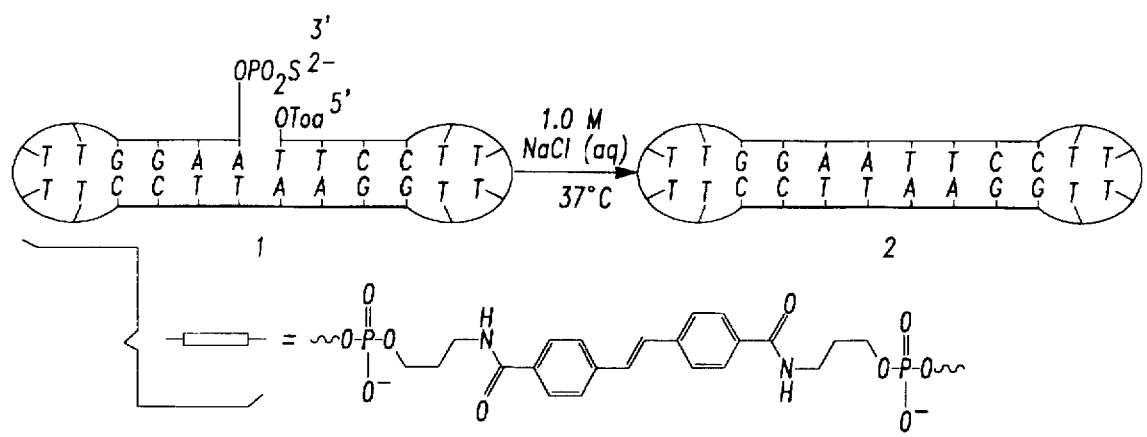
FIG. 3 demonstrates that the ligation chemistry can be employed to close a gap formed by a single linear oligonucleotide (SEQ ID NO:5) that folds to form a nicked dumbbell. The structure of the reactant and product is given in FIG. 1.

The conditions for ligation of two linear oligonucleotides on a template are indicated in FIG. 1. Cyclization of oligomers 1 (FIG. 3) and 3 (FIG. 6) was carried out with 1.3 micromolar oligonucleotide in 1 mL of aqueous buffer (pH 7.2, 30 mM phosphate, 1M NaCl) at 37° C. Samples were removed for analysis at the indicated times. The reaction of oligomer 5 (3.45 micromolar, 15% excess) with 6 (3.0 micromolar)(FIG. 9) was carried out in the same way at 35° C.

Oligomer Synthesis

Phosphitilation of 5'-O-tosylthymidine and of n-(dimethyltrityoxypropyl)-N'-(3-hydroxylpropyl) stilbene-4,4'-dicarboxamide was carried out by the standard procedure developed by Barone et al., (1984). Oligonucleotide 3'-phosphorothioates were prepared as described by Herrlein et al., (1994). Expedite phosphoramidite reagents (Millipore Corp.) were employed in synthesizing the oligonucleotides containing a tosyl group and products were deprotected with concentrated ammonium hydroxide (3) minutes at 55° C. followed by 1.5 hours at room temperature). For synthesis of other oligomers, standard N-benzoyl protected nucleoside phosphoramidite reagents were used, and the oligomer were deprotected by heating with ammonium hydroxide for 5 hours at 55° C. In both cases the ammoniacal solutions were concentrated to remove ammonia and the residue taken up in buffer for analysis and purification by RP HPLC. The purified products were also analyzed by IE HPLC.

EXAMPLES

Example 1

Although possessing two interactive functional groups, oligomer 1 (FIG. 3) could be readily isolated. It was stable to lyophilization conditions, to storage for ten days at −20° C., and to concentrated ammonium hydroxide at 37° C. for 2 hours.

On the other hand, oligomer 1 afforded an easily isolatable product, 2, (FIG. 3), in high yield (>94%) on standing for two hours in aqueous 1M NaCl. No further reaction occurred on standing at 37° C. for two more hours. The residual peak at 20.1 minutes in the HPLC profile (FIG. 5) probably stems from a small amount of an oligonucleotide 3'-phosphate in the sample of the 3'-thiophosphate.

Figure 4:
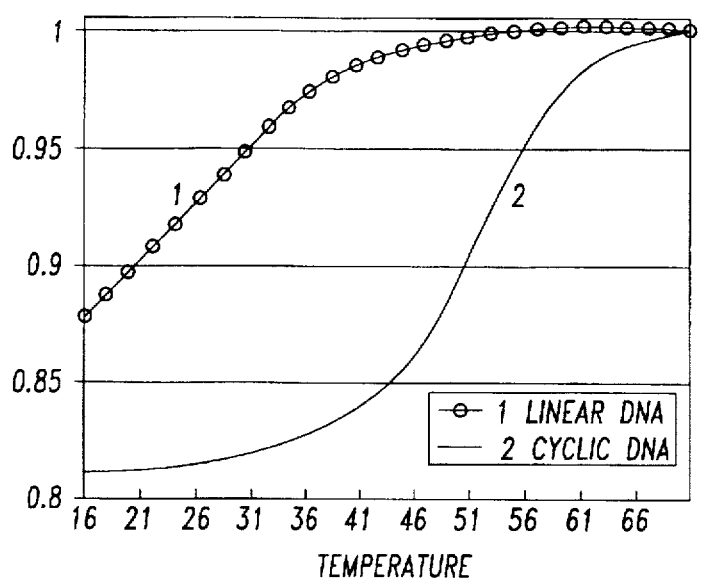
FIG. 4 is a graph illustrating melting curves for the compounds in FIG. 3 and shows that the termini of the oligonucleotide have indeed been linked covalently, the dissociation temperature (Tm) for the gapped dumbbell before ligation is below 26° C. in 50% ethanol/water (1M NaCl, pH 7.1). Under the same conditions, the Tm value for the closed dumbbell is >50° C.
Figure 5:
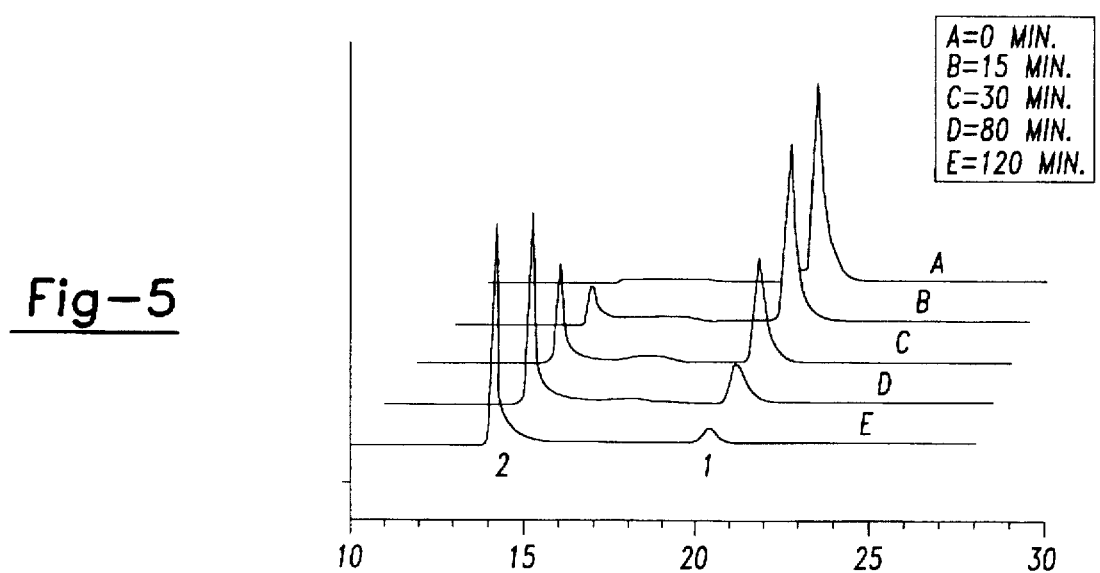
FIG. 5 illustrates the reversed phase HPLC (high performance liquid chromatography) profiles for the compounds of FIG. 3 and shows that the reaction is almost complete within two hours at 370° C. Additionally.
Figure 6:
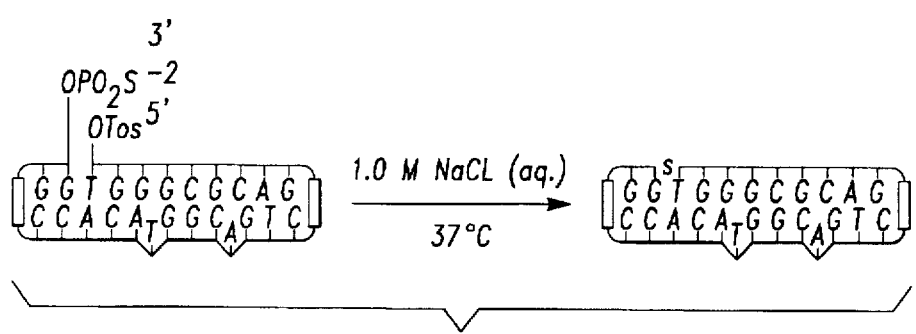
FIG. 6 shows the ligation chemistry applied to closure of a ring containing unusual base pairs (G:A and G:G) as well as nucleotide bulges (T and A) and two non-nucleotide bridges containing stilbenedicarboxamide units (see FIG. 3 for the structure for the bridges). Formula 4 represents the cyclic, ligated product, where s represents the internucleoside link —OP(O) (O⁻)S—. This compound (SEQ ID NO:6) is a small, conjugated deoxyribonucleotide mimic of a section of a Rev binding element of the HIV-1 genome.

Under the same conditions, no coupling was observed within 24 hours for a pair of non-hybridizing oligonucleotides in which one was terminated by a 3'-thiophosphoryl group and the other by a 5'-O-tosyl group. Strong evidence that the product from the reaction of 1 is a cyclic oligonucleotide was provided by its resistance to hydrolysis by alkaline phosphatase and T4 DNA polymerase. A control oligonucleotide 3'-phosphorothioate was degraded under the same conditions. (Gao et al., 1994; Erie et al., 1989). Other evidence for cyclization was provided by the large shift in retention time on RP HPLC (see FIG. 5). The relatively short elution time on ion exchange HPLC at pH 12 (33.9 minutes for oligomer 2 compared to 35.6 minutes for oligomer 1), is also consistent with cyclization and inconsistent with polymerization. Finally, denaturation curves show that oligomer 1 (Tm 45° C.) had been converted to a much more stable base-stacked structure (Tm~86° C.) as shown in FIG. 4. The shift in Tm for the nicked relative to the dumbbell structure (41° C.) corresponds to that reported by Ashley and Kushlan (1991) for cyclization of d-TTCCTTTTGGAATTCCTTTTGGAAp (SEQ ID NO:5) induced by a carbodiimide. In their case only a 30% yield of the cyclic product was isolated from a four day reaction.

Experiments with isolated samples showed that the phosphothio link in oligomer 2 resists attack by concentrated ammonium hydroxide (four hours at 55° C.) or 80% aqueous acetic acid (one hour at room temperature).

Example 2

A less favorable system for ligation is presented by compound 3 (FIG. 3), which may be considered a deoxyribonucleotide mimic of a section of a Rev binding element in the HIV-1 genome (Giver et al., 1993). The organized conformation for this conjugate would be expected to have two nucleotide bulges (dT and dA) and two unusual base pairs (dG:dA and dG:dG) as well as short base-paired stem regions. Although a stilbenedicarboxamide bridge helps stabilize a folded conformation, (Letsinger and Wu, 1995) the broad melting curve for compound 3 (FIG. 8) suggests considerable fraying of the hybridized strands.

Figure 7:
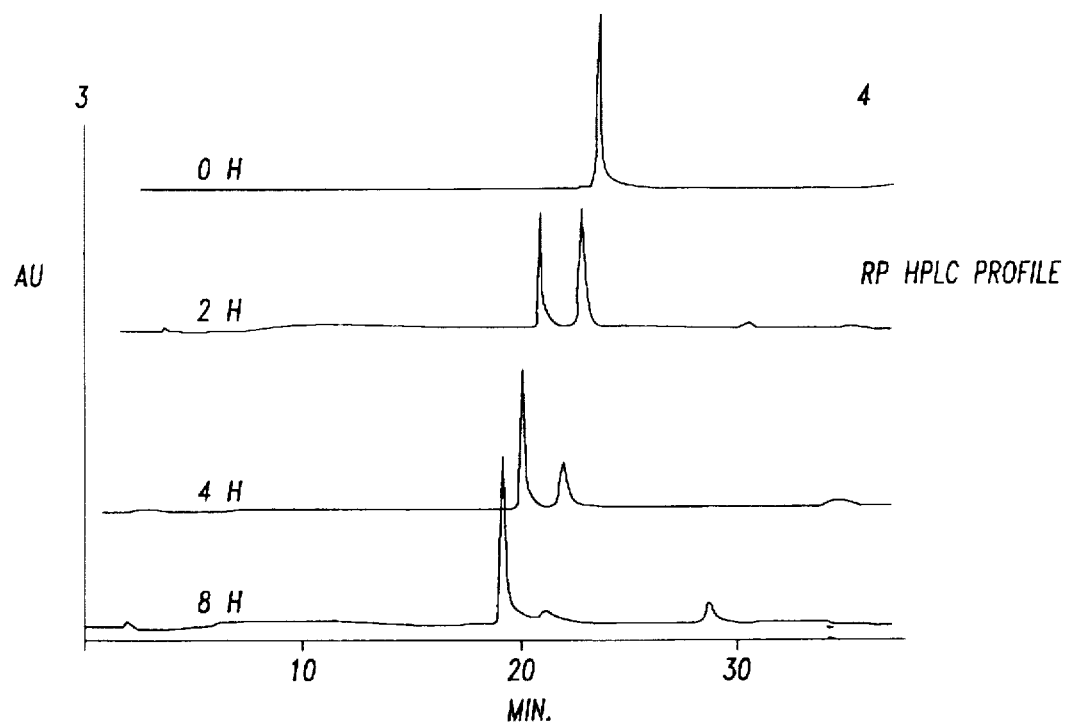
FIG. 7 illustrates the RP HPLC profiles in FIG. 6 and shows that the reaction proceeds well in spite of the nucleotide mismatches.
Figure 8:
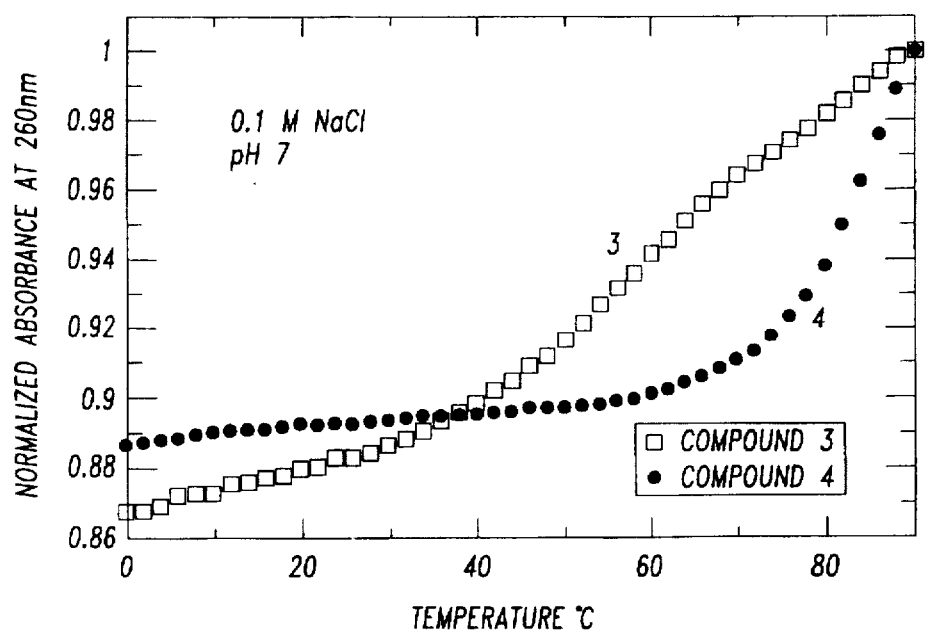
FIG. 8 illustrates the melting curve for the compounds of FIG. 6 demonstrating that the ring closure affords a small oligonucleotide domain that is unusually stable considering the base pairing (Tm>80° C. in 0.1M NaCl)

Nevertheless, ligation in 1M aqueous NaCl proceeded efficiently, affording oligonucleotide 4 (96%) within eight hours (see FIG. 7). As for cyclization of oligomer 1, the product eluted faster than the reactant on RP HPLC (19.1 minutes for compound 4, 21.0 minutes for compound 3) and on ion exchange HPLC at pH 12 (36.2 minutes for compound 4, 38.3 minutes for compound 3), and exhibited much greater stability than the reactant on thermal denaturation (FIG. 8).

The extraordinarily high melting temperature for compound 4 (Tm~84° C., 0.1M NaCl), a compound with a short nucleotide sequence containing unmatched bases, demonstrates the stabilizing effect of stilbenedicarboxamide groups that cap both ends of a duplex segment and the advantage of locking the termini of the oligonucleotide together by the ligation reaction.

Example 3

Figure 9:
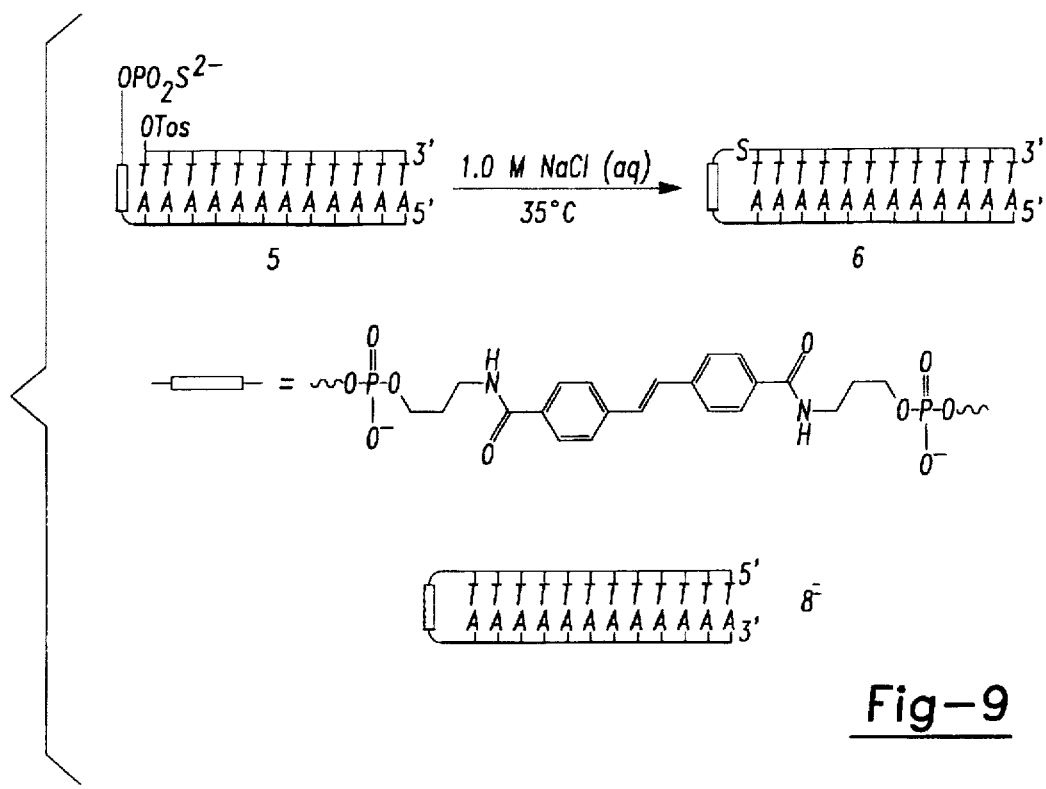
FIG. 9 illustrates the ligation of two oligonucleotides by (SEQ ID NOS:7 and 8) closing a non-nucleotide cap at the end of a double helix.
Figure 10:
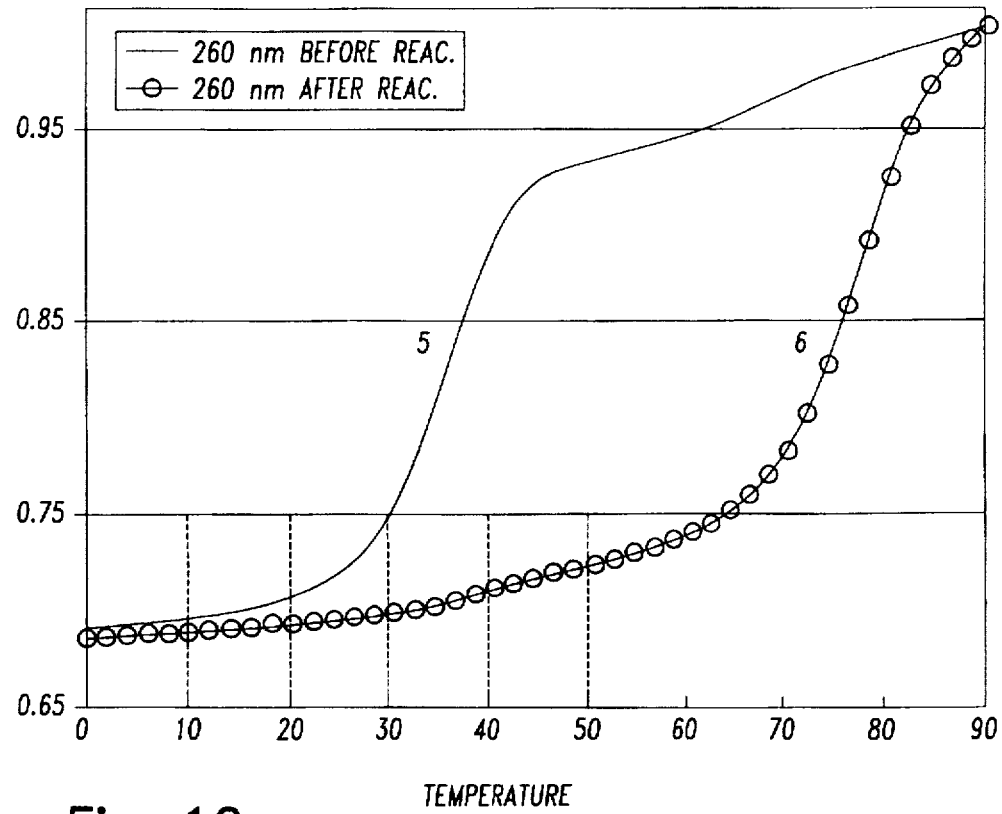
FIG. 10 illustrates melting curves for the products formed from oligonucleotides 5 and 6 in FIG. 9, showing that the ligation proceeds well to give the hairpin structure in ~90% yield within eight hours. The large increase in the Tm value (from about 35° C. for the reactant to ~75° C. for the product) is consistent with formation of a covalent hairpin oligonucleotide complex containing a stilbenedicarboxamide bridge (see Letsinger and Wu, 1995)

The third system (oligonucleotides 5+6) FIG. 9) was selected to see if the tosyl displacement reaction could be used to close an organic bridge across the end of an oligonucleotide duplex. The expected product, 6 (FIG. 9), is closely related to an oligonucleotide conjugate, $dT_{12}$-

Figure 11:
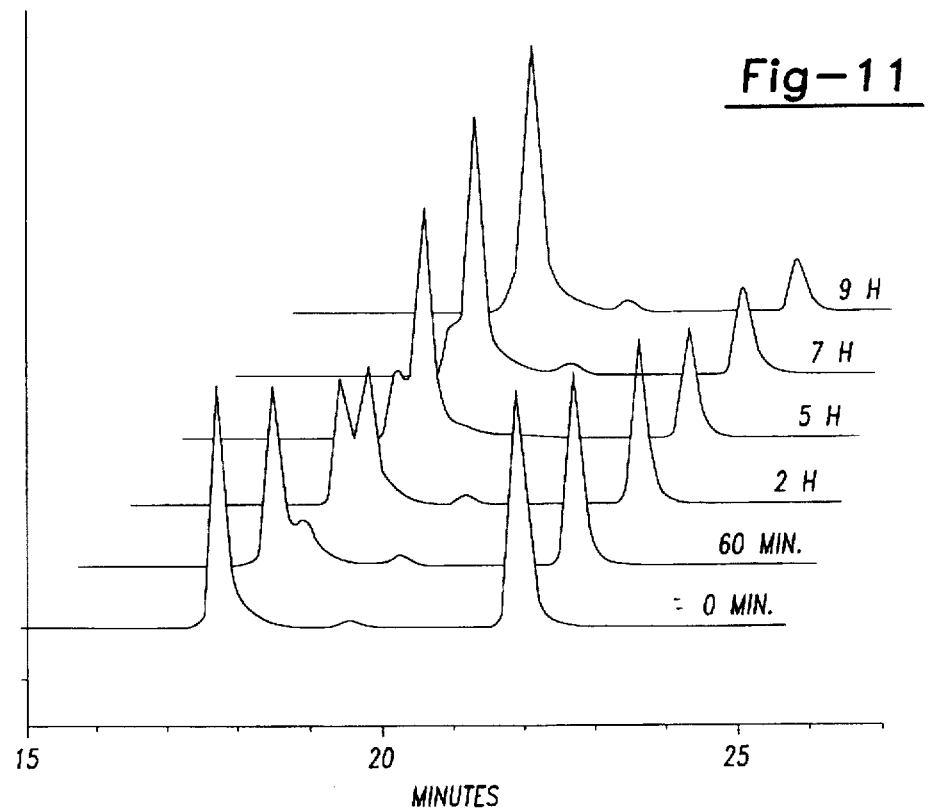
FIG. 11 illustrates the RP HPLC profiles for the conversion of compound 5+6 of FIG. 9 to a hairpin oligonucleotide conjugate.

{stilbenedicarboxamide-bridge}-dT$_{12}$, designated as compound 8 and shown in FIG. 9, prepared by stepwise synthesis and found to fold to a hairpin structure (Tm 64° C.) (Letsinger and Wu, 1995). The reaction of oligonucleotides 5 with 6 was somewhat slower than cyclization of oligomer 1; however it proceeded smoothly to give a single product (FIG. 11). In accord with a covalent hairpin structure for compound 7, the product exhibited a high Tm value (69° C. as compared to 35° C. for oligonucleotides 5+6) (FIG. 10), elution times on RP HPLC and IE HPLC indistinguishable from values for reference compound 8, and a fluorescence band at 386 nm characteristic for an unperturbed stilbene chromophore. Absence of a band in the 445 nm region indicated absence of ligation products that associate as a bimolecular duplex. (Letsinger et al., 1994; Lewis et al., 1995).

The above examples demonstrate that the tosyl displacement reaction provides an effective means for covalently linking self-assembled oligonucleotide domains. The coupling depends strongly on organization of the component blocks, but the latitude and the geometrical constraints are sufficient to permit efficient coupling in oligonucleotides systems that differ substantially from those conventionally employed in ligation. That is, linear oligonucleotides, dumbbell oligonucleotides, cyclized oligonucleotides containing mismatched bases, hairpin conjugates, and the like can be formed in accordance with the present invention utilizing efficient and effective coupling reactions.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES

Ashley and Kushlan, *Biochemistry* 30, 2927–2933 (1991).
Barone et al., *Nucleic Acids Res.*, 12, 4051–4061 (1984).
Bischofberger and Wagner, (1992).
Chamrvedi and Letsinger, *Am. Chem. Soc.*, meeting in Anaheim, Calif., April 1995.
Chladek and Nagyvary, *J Am. Chem. Soc.*, 94, 2079–2085 (1972).
Cook, *J. Am. Chem. Soc.* 92, 190–195 (1970).
Crooke and Lebleu, Ed., *Antisense Research and Application* (CRC Press, Boca Raton, Fla.) (1993).
Durand et al., *Nucleic Acids Res.* 18, 6353–6359, (1992).
Erie, et al., *Biochemistry*, 26, 7150–71, (1989).
Fu, et al., *Am. Chem. Soc.* 116, 4591–4598 (1994).
Gao, et al., *Bioconjugate Chem.* 5, 445–453 (1994).
Giver, et al., *Nucleic Acids Res.*, 21, 5509–5516, (1993).
Goodwin and Lynn, (1992).
Gryaznov, *Nucleosides and Nucleotides*, 14:1019–1022 (1995).
Gryaznov and Letsinger, (1991).
Gryaznov and Letsinger, *J. Am. Chem. Soc.* 115, 3808–3809 (1993).
Gryaznov and Letsinger, *Nucleic Acids Res.* 21, 1403–1408 (1993).
Gryaznov, et al., *Nucleic Acids Res.*, 22:2366–2369 (1994).
Helene and Touleme, *Biochem. Biophys. Acta*, pp.99–125 (1990)
Heller and Tullis, *Nanotechnology*, 2:165–171 (1991).
Herrlein and Letsinger, *Nucleic Acids Res.*, 22, 5076–5078 (1994).
Kool, *J. Am. Chem. Soc.*, 113, 6265–6266 (1991).
Kresse et al., *Nucleic Acids Res.*, 2, 1–9 (1975).
Letsinger, (1993).
Letsinger and Wu, *Am. Chem. Soc.* 116, 811–812, (1994).
Letsinger and Wu, *J. Am. Chem. Soc.*, in press.
Lewis et al., *Am. Chem. Soc.* in press, (1995).
Lowe, *Clinica Chimica Acta*, 157:1–32, (1986).
Luebke and Dervan, *J. Am. Chem. Soc.*, 113:7447–7448 (1991).
Luebke and Dervan, *Nucleic Acids Res.*, 20:3005–3009 (1992).
Ma et al., *Biochemistry*, 32, 1751–1758 (1993).
Meade and Kayyem, *Agnew. Chem. Int. Ed. Engl.* 34, 352–354 (1995).
Paterson. D., *Scientific American*, 33–34 (1995).
Salunke et al., *J. Am. Chem. Soc.* 114, 8768–8772 (1992).
Shabarova, *Biochemie*, 70, 1323–1334 (1988).
Thompson et al., *Nucleic Acids Res.* 21: 5600–5603 (1993).
Uhlman and Peyman, *Chem. Rev.* 90:544–548, (1990).
Urdea et al., *Nucleic Acids Res.* 16:4937–4956 (1988).
Wang and Yanagawa, *Biochemistry*, 25:7423–7430 (1986).

---

What is claimed is:

1. A method of covalently autoligating self-assembled oligonucleotide segments by displacing a 5' displaceable group by a 3' thiophosphoryl group to spontaneously form an —OP (O) ($O^{3+}$) S— internucleoside linkage.

2. A method of claim 1 further including the steps of bringing the 5' displaceable group and 3'-thiophosphoryl group into proximity, the 3' thiophosphoryl group then displacing the displaceable group to form the internucleoside linkage.

3. A method as set forth in claim 2 wherein the 3'-thiophosphoryl group and the 5' displaceable group are on the same oligonucleotide.

4. A method as set forth in claim 3 wherein said forming step is further defined as forming a cyclized oligonucleotide containing non-nucleotide bridges.

5. A method as set forth in claim 3 wherein said forming step is further defined as forming a dumbbell oligonucleotide.

6. A method as set forth in claim 3 wherein said forming step is further defined as forming a cyclized nucleotide conjugate.

7. A method as set forth in claim 2 wherein the 3'-thiophosphoryl group and the 5' displaceable group are on different oligonucleotide strands.

8. A method as set forth in claim 1 wherein the displaceable group is selected from the group consisting of $Cl^-$, $Br^-$, $I^-$, and $RSO_3^-$ where R is phenyl or phenyl substituted with one to five atoms or groups comprising F,Cl,Br,I,alkyl (C1 to C6), nitro, cyano, sulfonyl and carbonyl, or R is alkyl with one to six carbons.

9. A method as set forth in claim 1 wherein the displaceable group is a hydrophobic tosyl group, said displacing step being further defined as displacing the 5'-O-tosyl group by a "3'-thiophosphoryl" group.

10. A method as set forth in claim 9 wherein the tosyl group is a 5'-O-p-toluenesulfonyl group, said displacing step being further defined as displacing the 5'-O-p-toluenesulfonyl group by the 3'-thiophosphoryl group.

* * * * *